US009662492B1

(12) United States Patent
Tucker et al.

(10) Patent No.: US 9,662,492 B1
(45) Date of Patent: May 30, 2017

(54) METHOD FOR TRANSCRANIAL NEUROSTIMULATION

(71) Applicant: Electrical Geodesics, Inc., Eugene, OR (US)

(72) Inventors: Don M. Tucker, Eugene, OR (US); Phan Luu, Eugene, OR (US); Sergei I. Turovets, Eugene, OR (US); Erik Anderson, Eugene, OR (US)

(73) Assignee: Electrical Geodesics, Inc., Eugene, OR (US)

( * ) Notice: Subject to any disclaimer, the term of this patent is extended or adjusted under 35 U.S.C. 154(b) by 238 days.

(21) Appl. No.: 14/339,881

(22) Filed: Jul. 24, 2014

(51) Int. Cl.
*A61N 2/00* (2006.01)
*A61N 1/36* (2006.01)
*A61B 5/053* (2006.01)

(52) U.S. Cl.
CPC .......... *A61N 1/36025* (2013.01); *A61B 5/053* (2013.01); *A61N 2/002* (2013.01)

(58) Field of Classification Search
CPC . A61N 1/00; A61N 2/00; A61N 2/002; A61N 2/004; A61N 2/006; A61N 2/008; A61N 2/02

USPC .................................................... 600/9–15
See application file for complete search history.

(56) References Cited

U.S. PATENT DOCUMENTS

| 8,494,627 | B2* | 7/2013 | Bikson | ............... | A61N 1/36025 607/2 |
| 2012/0245653 | A1* | 9/2012 | Bikson | ............... | A61N 1/36025 607/45 |

* cited by examiner

*Primary Examiner* — Samuel Gilbert
(74) *Attorney, Agent, or Firm* — Portland Intellectual Property, LLC (57) ABSTRACT

Method for transcranial neurostimulation. A target of neurons for transcranial stimulation or modulation is located within an impedance model of the brain, a model of a selected device to be used for producing an electric or magnetic field outside the brain is obtained and used, along with the impedance model, to compute respective virtual target stimulating current vectors representing target stimulating currents that would result from using the device in two distinct trial dispositions of the device, an image of the cortical surface at the target is obtained and used to compute a target normal vector, and a determination is made of which of the two virtual target stimulating current vectors has a greater component projecting at predetermined angles from the target normal vector.

8 Claims, 7 Drawing Sheets

METHOD FOR TRANSCRANIAL NEUROSTIMULATION

FIELD OF INVENTION

The present invention relates to methods for stimulating or modulating neural firing in the brain by applying electrical or magnetic fields to the surface of the head.

BACKGROUND

It is often desired to non-invasively stimulate or modulate neuronal firing in the brain by use of externally applied electric or magnetic forces.

Neurostimulation requires sufficiently large electric or magnetic force to provoke neuronal firing that would not otherwise occur, whereas neuromodulation is for controlling or influencing neuronal firing that occurs naturally (although often abnormally), and therefore employs forces of lesser magnitude. Both stimulation and modulation are used for research purposes, and modulation is particularly useful for therapeutic purposes such as for suppressing seizures in people with epilepsy.

The standard terminology used to refer to such methods does not distinguish between stimulation and modulation. Where electrical potentials are applied to the surface of the head to drive plate electrodes for injecting electrical currents into the head and brain, the methods are known as "transcranial current stimulation" or TCS; and where time-varying magnetic potentials are created outside the surface of the head for inducing electrical currents to flow inside the head and brain, the methods are known as "transcranial magnetic stimulation" or TMS. So, the terms "TCS" and "TMS" refer to neurostimulation or neuromodulation, or both, and for purposes herein, the term "stimulate" is intended to refer to either stimulating or modulating.

TCS methods are distinguished between those that inject DC currents, referred to as "transcranial direct current stimulation" or TDCS, and those that inject AC or pulsed currents, referred to as "transcranial alternating current stimulation" or TACS. Since TMS requires time-varying magnetic fields, there is nothing analogous to TDCS in TMS.

U.S. Pat. No. 7,190,826 describes a geodesic sensor net which may employed to provide a dense array of electrodes, e.g., 256, for use in TCS. The electrodes are electronically selected in desired current source/current sink (hereinafter "source/sink") combinations at the head surface to provide for the stimulation/modulation. The electrodes may be replaced with, or used in combination with, magnetic coils for practicing TMS.

TMS methods employ one coil or one pair of coils which may be thought of as one-for-one substitutes for a source/sink pair of electrodes used in TCS. Currents flowing through the coils produce corresponding magnetic fields, and in particular, time-varying currents produce corresponding time-varying magnetic fields which induce electric currents to flow in the nearby circuitry defined by the neural pathways in the brain. So TMS serves the same purpose served by TCS.

The target of the stimulation/modulation is one or more "patches" of neurons, which are local groups of neurons that "fire together" and can therefore be treated as being single sources of electrical activity.

U.S. Pat. No. 6,594,521 describes a TCS method for determining how to stimulate a target patch of neurons in the brain, by replicating the potential distribution or lead-field projection that is measured at the head surface as a result of un-stimulated activity from the target, based on principles of Lorentz reciprocity.

SUMMARY

Methods for transcranial neural stimulation are disclosed herein. A first computational method provides for determining how to stimulate a target patch of neurons. An impedance model of the brain may be obtained by use of standard methods, and the target location may be identified within the impedance model, also by use of standard methods.

Further, a device model of a predetermined device capable of producing electric or magnetic fields outside the brain may be obtained, and the device model may be used with the impedance model to compute a first virtual target stimulating current vector at the target location resulting from virtually using the device as disposed in a first trial disposition outside the brain to produce a virtual electric or magnetic field, and to compute a second virtual target stimulating current vector at the target location resulting from virtually using the device as disposed in a second trial disposition outside the brain distinct from the first trial disposition to produce a virtual electric or magnetic field.

Still further, an image of the cortical surface of the brain at the target location may be obtained. Then, the method may include using the image for computing a target normal vector normal to the cortical surface at the target location, and determining which of the first and second virtual target stimulating current vectors has a greater component of virtual target stimulating current projecting at a predetermined first polar angle between zero and 45 degrees with reference to a spherical coordinate system taking the direction of the target normal vector as the zenith.

With the polar angle at zero, the first method allows for selecting between the first and second trial dispositions of the device based, at least in part, on favoring that one of the first and second virtual target stimulating current vectors which has the greater said component of target stimulating current. The method may be used for stimulating the target patch of neurons by actually using the device in the selected trial disposition to produce a real electric or magnetic field.

In a second computational method for determining how to stimulate a target patch of neurons, the first method may be modified to include using the device model and the impedance model to compute a first virtual "first non-target" stimulating current vector at a first non-target location distinct from the target location resulting from virtually using the device as disposed in the first trial disposition, and to compute a second virtual "first non-target" stimulating current vector at the first non-target location resulting from virtually using the device as disposed in the second trial disposition.

Further, the image in the second computational method includes the first non-target. Then, the method may include using the image for computing a "first non-target" normal vector normal to the cortical surface at the first non-target location, and determining which of the first and second virtual "first non-target" stimulating current vectors has a lesser component of virtual "first non-target" stimulating current projecting parallel to the "first non-target" normal vector.

With the polar angle at zero, the second method allows for selecting between the first and second trial dispositions of the device based, at least in part, on balancing between favoring that one of the first and second virtual target stimulating current vectors which has the greater component of virtual target stimulating current and favoring that one of the first and second virtual "first non-target" stimulating current vectors which has the lesser component of virtual "first non-target" stimulating current.

In a third computational method for determining how to stimulate a target patch of neurons, the second method may be modified to include using the device model and the impedance model to compute a first virtual "second non-target" stimulating current vector at a second non-target location distinct from the target location and the first non-target location, the first virtual "second non-target" stimulating current resulting from virtually using the device as disposed in the first trial disposition, and to compute a second virtual "second non-target" stimulating current vector at the second non-target location resulting from virtually using the device as disposed in the second trial disposition.

Further, the image in the third computational method includes the second non-target. Then, the method may include using the image for computing a "second non-target" normal vector normal to the cortical surface at the second non-target location, and determining which of the first and second virtual "second non-target" stimulating current vectors has a lesser component of virtual "second non-target" stimulating current projecting parallel to the "second non-target" normal vector.

With the polar angle at zero, the third method allows for selecting between the first and second trial dispositions of the device based, at least in part, on balancing between favoring that one of the first and second virtual target stimulating current vectors which has the greater component of virtual target stimulating current and favoring that one of the first and second virtual "second non-target" stimulating current vectors which has the lesser component of virtual "second non-target" stimulating current. The method may be used for stimulating the target patch of neurons by actually using the device at the selected trial disposition to produce a real electric or magnetic field over a first time period, and actually using the device at the second selected trial disposition to produce a real electric or magnetic field over a second time period distinct from the first time period.

In a fourth computational method for determining how to stimulate a target patch of neurons, the first method employs polar angles greater than zero degrees, and may be modified to include selecting between the first and second trial dispositions of the device based, at least in part, on favoring that one of the first and second virtual target stimulating current vectors which has a greater component of virtual target stimulating current projecting at the first polar angle at a predetermined first angle of azimuth.

Further, the device model may be used with the impedance model to compute a third virtual target stimulating current vector at the target location resulting from virtually using the device as disposed in a third trial disposition outside the brain distinct from the first and second trial dispositions to produce a virtual electric or magnetic field, and to compute a fourth virtual target stimulating current vector at the target location resulting from virtually using the device as disposed in a fourth trial disposition outside the brain distinct from the first, second, and third trial dispositions to produce a virtual electric or magnetic field.

The fourth method allows for selecting between the third and fourth trial dispositions of the device based, at least in part, on favoring that one of the third and fourth virtual target stimulating current vectors which has a greater component of virtual target stimulating current projecting at a predetermined second polar angle of at least 5 degrees but less than or equal to 45 degrees at a second angle of azimuth distinct from the first angle of azimuth. The method may be used for stimulating the target patch of neurons by actually using the device at the selected one of the first and second trial dispositions to produce a real electric or magnetic field over a first time period, and actually using the device at the selected one of the third and fourth trial dispositions to produce a real electric or magnetic field over a second time period distinct from the first time period.

In a modified version of the fourth method for determining how to stimulate a target patch of neurons, the device and impedance models may be used to compute a first virtual non-target stimulating current vector at a non-target location distinct from the target location, the first virtual non-target stimulating current resulting from virtually using the device as disposed in the first trial disposition, and to compute a second virtual non-target stimulating current vector at the non-target location resulting from virtually using the device as disposed in the second trial disposition.

Further, the image in the modified version of the fourth method includes the non-target. Then, the method may include using the image for computing a non-target normal vector normal to the cortical surface at the non-target location, and determining which of the first and second virtual non-target stimulating current vectors has a lesser component of virtual non-target stimulating current projecting parallel to the non-target normal vector.

The modified version of the fourth method allows for selecting between the first and second trial dispositions of the device based in part on balancing between favoring that one of the first and second virtual target stimulating current vectors which has the greater component of target stimulating current projecting at said first polar angle at a predetermined first angle of azimuth, and favoring that one of the first and second virtual target stimulating current vectors which has the lesser component of virtual non-target stimulating current.

It is to be understood that this summary is provided as a means of generally determining what follows in the drawings and detailed description and is not intended to limit the scope of the invention. Objects, features and advantages of the invention will be readily understood upon consideration of the following detailed description taken in conjunction with the accompanying drawings.

DETAILED DESCRIPTION

As noted above, a target patch of neurons in a subject's brain may be stimulated by use of TCS methods that replicate the potential distribution measured at the surface of the subject's head that is produced by neural activity at that target as taught in U.S. Pat. No. 6,594,521. It may be appreciated that the same principles will apply to TMS methods as well.

Alternatively, the potential distribution may be determined by a combination of imaging and computation—by imaging the head to determine the precise locations of the various tissue types therein (scalp, skull, cerebrospinal fluid, gray matter, and white matter), such as by magnetic resonance imaging (MRI); by identifying those tissue types, preferably using the automated tissue segmentation method taught in U.S. Pat. No. 8,478,011, and using the characteristic impedance values of the tissue types to construct a computerized electrical impedance model of the head; by determining the location of the target patch by use of functional imaging techniques such as functional magnetic resonance imaging (fMRI), positron emission tomography (PET), or electroencephalography (EEG) and locating the target patch in the impedance model; and by running a number of computerized trials in which the relative magnitude of computed, hypothetical or "virtual" stimulating currents at the target patch are compared for various computed, hypothetical or "virtual" source/sink combinations.

"Imaging" refers to any known methodology for obtaining one or more images, and an "image" may be in two or three dimensions. For example, in magnetic resonance imaging a number of two dimensional images are combined to form a single three dimensional image.

"Computation" is used herein, among other things, to model the results of performing hypothetical or "virtual" TCS or TMS.

Figure 1:
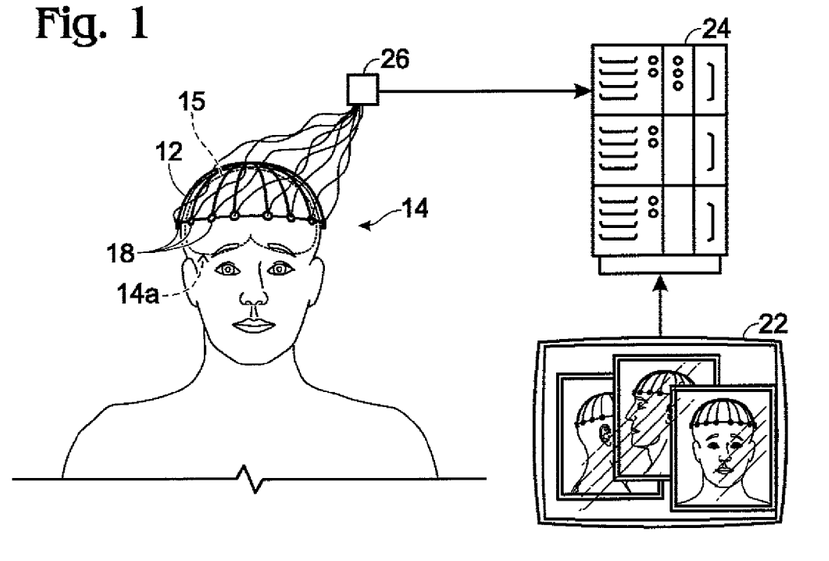
FIG. 1 is a schematic view of a system for performing TCS or TMS methods according to the present invention.

FIG. 1 shows a net 12 of electrodes applied to the head 14 of a human subject for performing real TCS of the subject's brain 14a, it being understood that the subject may be any animal. The electrode net 12 has an array of electrodes 18. Each electrode defines a distinct node of the net 12, the location of which can be measured by use of a photogrammetric system 22 as taught in U.S. Pat. No. 7,190,826. The electrodes may be driven by either a voltage or a current source 26 in electronically configurable or selectable source/sink pairs, as controlled by a computer system 24.

For performing real TMS, the net 12 may either include, or substitute for the respective electrodes 18, localized groups of one or more magnetic coils. The electrodes and/or coils are driven by the source 26 as is typical in the art.

Figure 2:
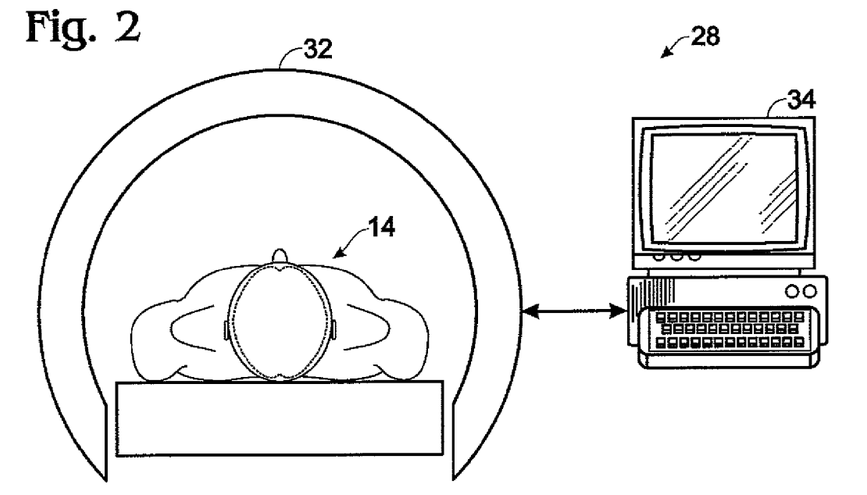
FIG. 2 is a schematic view of an imaging and computing system for performing methods according to the present invention.

FIG. 2 shows an imaging and computing system 28 for imaging at least the brain portion 14a of the subject's head. The imaging and computing system 28 typically includes a MRI device 32 and a computer system 34 for controlling the MRI device to produce image data and constructing two dimensional and/or three dimensional images from the image data.

The computer systems 24 and 34 may be the same computer system, serving the purposes required of both, and may also be used for performing the computations described herein; however, separate computers or computer systems may be used for any or all of these purposes. Also, either or both the computer systems 24 and 34 may be a single computer, such as a PC or Macintosh, or a part of a larger network of computers connected by a local area network or a wide area network such as the Internet.

The computerized trials employ computer models of the electrical/magnetic functioning of the electrodes and/or coils.

It is convenient for purposes herein to refer to one source/sink combination as a single "device" for producing an electric or magnetic field, to allow for using the same terminology in describing both TCS and TMS methods. TMS presents the simple case, where the device is one or more coils localized at one node of the net 12. The device can be referred to as being disposed, or having a disposition, at the location of the node. In the case of TCS, where one device is defined as a being a source/sink combination, the device is disposed, or has a disposition, at more than one node, i.e., the node of the net 12 at which the source electrode is located and the node of the net 12 at which the sink electrode is located.

The term "trial disposition" refers to "virtual" or computer-modeled dispositions, and the process of running a computerized trial of using a device in a given trial disposition may be referred to as "virtually using" the device in that disposition, as distinct from actually using a real device having that disposition to produce a real electric or magnetic field.

Hereinafter for ease of discussion the invention will be described for use in TCS methods, it being understood that the principles of the invention apply equally to TMS methods.

It is an insight of the present joint inventors to apply an additional constraint on the above described computational method, based on recognizing that the target patch is located on the cortical surface; that the neurons in the patch are dipoles aligned normal to the cortical surface; and that the neurons in the cortical patch are stimulated to the extent that the stimulating current has a component that is normal to the cortical surface at the target patch.

Figure 3:
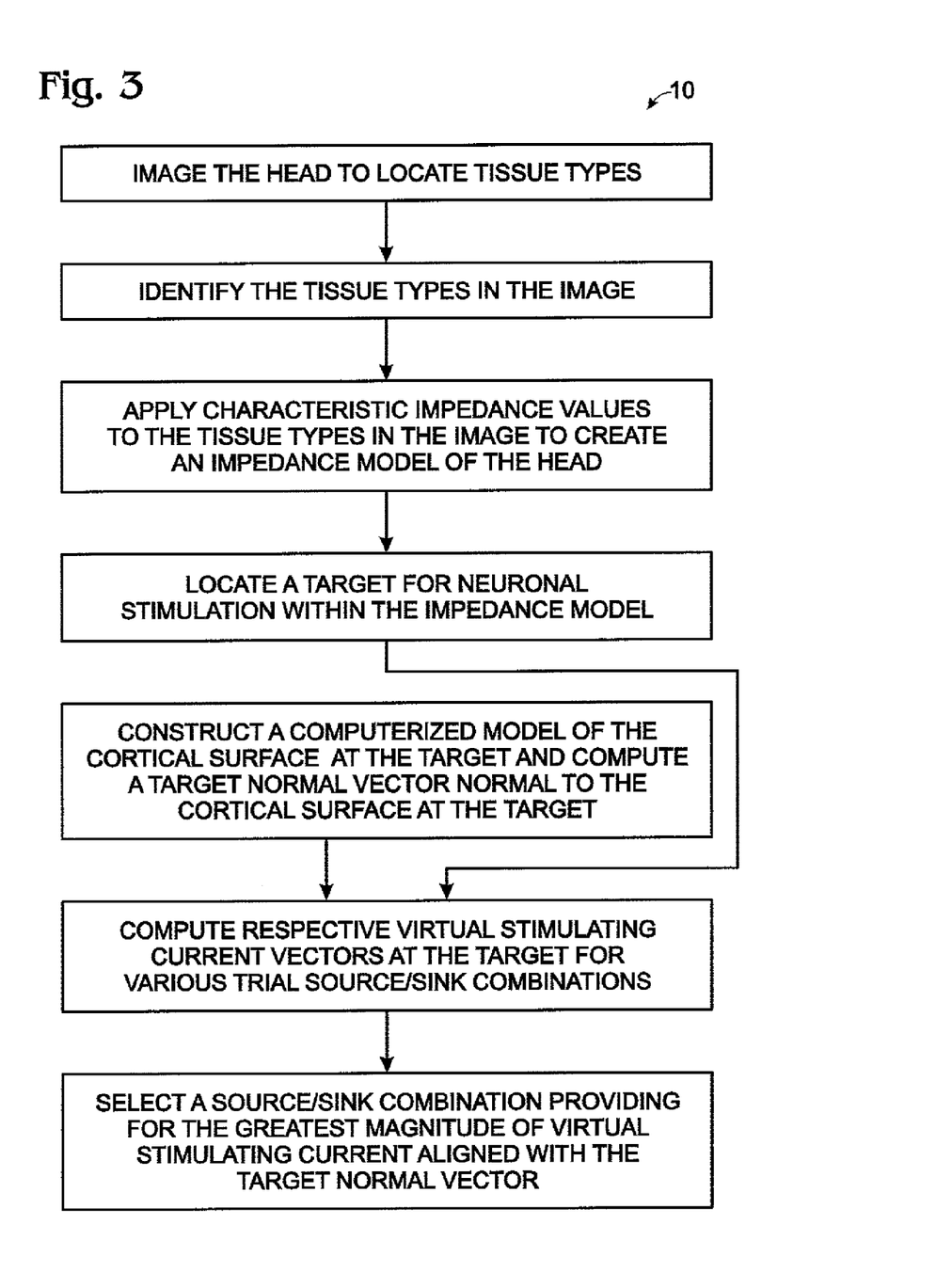
FIG. 3 is flow chart of a first computational method for determining how to stimulate a target patch of neurons on the cortical surface according to the present invention.

Based on these recognitions a first, basic computational method 10 for determining how to stimulate a target patch of neurons on the cortical surface (indicated as 15 in FIG. 1) may be provided according to the present invention, in which the MR head image is used, in addition to obtaining an impedance model of the head, or a different head image could be used, to locate the cortical surface. Then, a computerized or virtual model of the cortical surface generally, or of the target specifically, may be constructed and the computer may compute a target normal vector that is normal to the cortical surface at the target. The computerized trials include computing that magnitude of the virtual stimulating current at the target patch which is aligned normal to the cortex at that location. Then, an optimized source/sink pattern or trial device disposition for stimulating the target may be obtained by selecting that which provides for the greatest magnitude of virtual stimulating current aligned with the target normal. FIG. 3 is a flow chart of the basic method 10.

It is not essential for the head image to provide for more than a brain image. No more is needed for identifying the cortical surface, and no more is needed for constructing the impedance model because the scalp and skull can reasonably accurately be modeled on general principles without need for an image of the specific subject's head.

According to the invention, the normal to the cortical surface at a given patch of neurons can be taken as an average of the normal vectors at each of the infinitesimal areas of cortical surface within that patch, which can be approximated on a computer system by use of standard numerical methods. Alternatively according to the invention, the cortical surface may be divided (tessellated) into triangles having the approximate size of a single patch (about 1 cm$^2$), and the normal vector for the patch is taken as the normal to the triangle. Other geometric shapes effective for tiling the cortical surface could be used.

It is a further insight of the present joint inventors that optimizing the stimulation of a target will often result in undesirable levels of current being delivered to non-target areas as well, and that that this problem can be alleviated by modifying the basic computational method described above.

Figure 4:
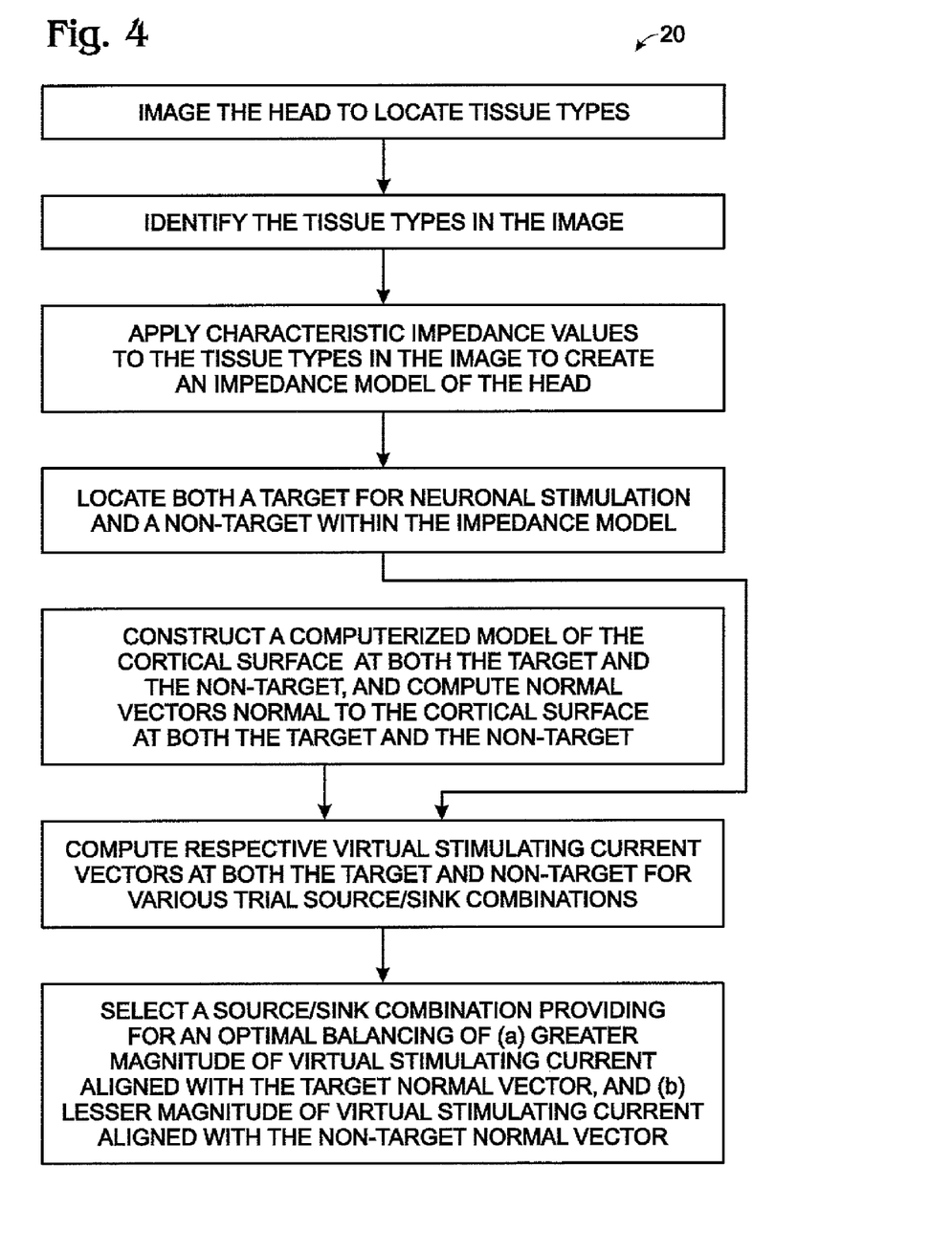
FIG. 4 is a flow chart of a second computational method for determining how to stimulate a target patch of neurons on the cortical surface according to the present invention.

Particularly, the computerized trials are modified according to the invention in a second computational method 20 according to the invention that considers the effect of the virtual stimulating current on non-target as well as target areas, by selecting a virtual source/sink pattern or trial device disposition that is optimal for both maximizing the dot product of the virtual current with vectors normal to the cortical surface at the target patch, and minimizing the dot product of the virtual current with vectors normal to the cortical surface at the one or more non-target patches. FIG. 4 is a flow chart of the method 20.

Computationally, optimizing for stimulation of a target patch relative to one or more non-target patches according to the invention may be performed by minimizing a cost function that recognizes, for each trial source/sink combination, that the desired maximized dot product of the virtual stimulating current and the normal vector at the target patch has an associated cost represented by the dot product of that virtual stimulating current and the normal vectors at one or more respective non-target patches.

The head impedance model may be used to compute the pathways through which any hypothetical stimulating current will flow, including the component of the flow that is normal to the cortical surface at both the target and the one or more non-target patches.

It is still a further insight of the present joint inventors that, for any given target patch there are a number choices for the one or more non-target patches, and thus according to a third computational method 30 according to the invention, a set of trial device dispositions may be identified, with each member of the set being optimized for maximizing the dot product of the virtual stimulating current and the normal vector at the target patch relative to one or more non-target patches that are different from the one or more non-target patches for which the other trial device dispositions in the same set have been optimized. Then according to the invention, actual stimulation of the target may be further optimized by cycling through real dispositions of the devices corresponding to all or a selected subset of the trial device dispositions in the set, in a sequence. For example, if there are 30 optimized trial device dispositions in a set, each being optimized to minimize cost at a different one of 30 non-target patches, each of 30 real device dispositions corresponding respectively to the 30 trial device dispositions may be utilized in turn to source and sink stimulating current for one minute according to the invention, so as to provide for a total stimulation period of 30 minutes.

Figure 5A:
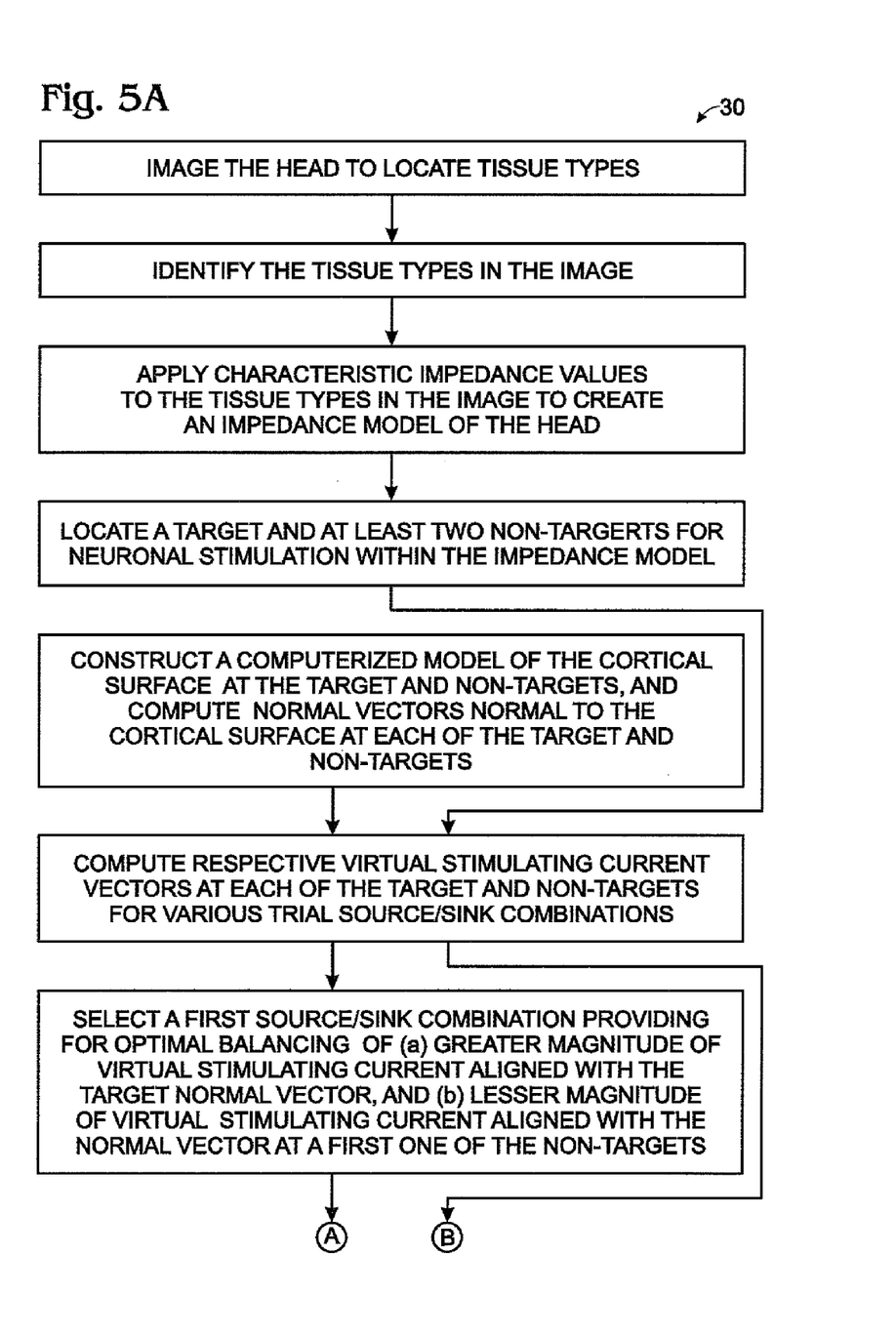
FIG. 5A is a flow chart of a third computational method for determining how to stimulate a target patch of neurons on the cortical surface according to the present invention.
Figure 5B:
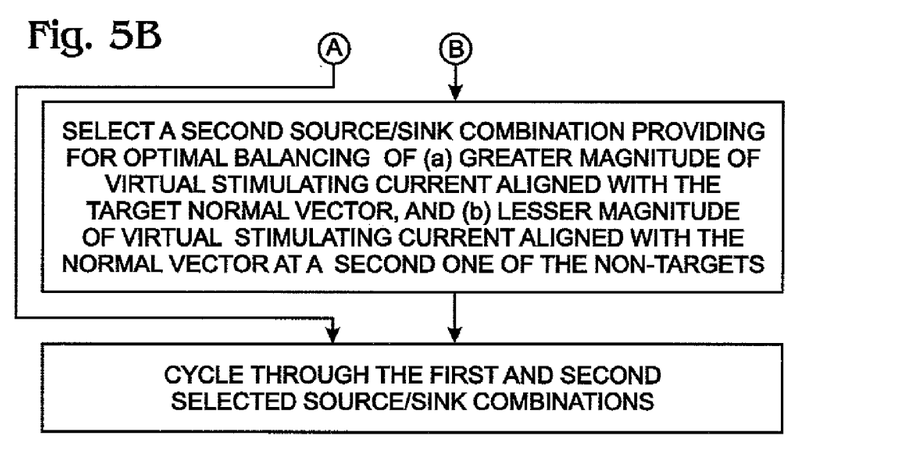
FIG. 5B is a continuation of FIG. 5A.

FIGS. 5A and 5B are a flow chart showing how the method 30 applies in a simple case where there are two members in the set of trial dispositions, it being understood that the method employs the same steps if the sets of trial dispositions have more than two members.

Figure 6A:
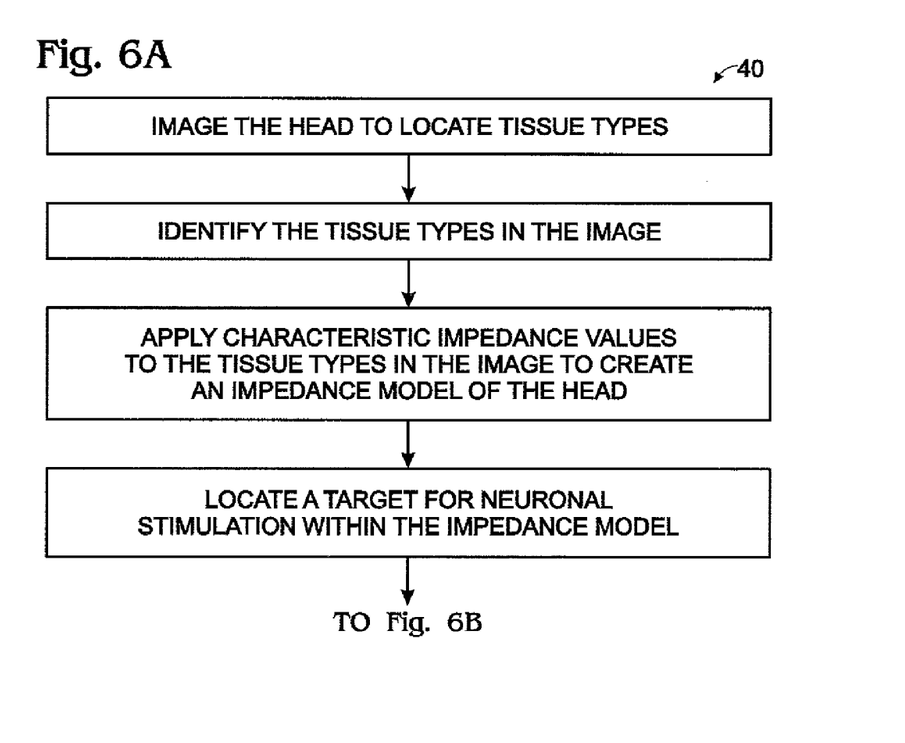
FIG. 6A is a flow chart of a fourth computational method for determining how to stimulate a target patch of neurons on the cortical surface according to the present invention.
Figure 6B:
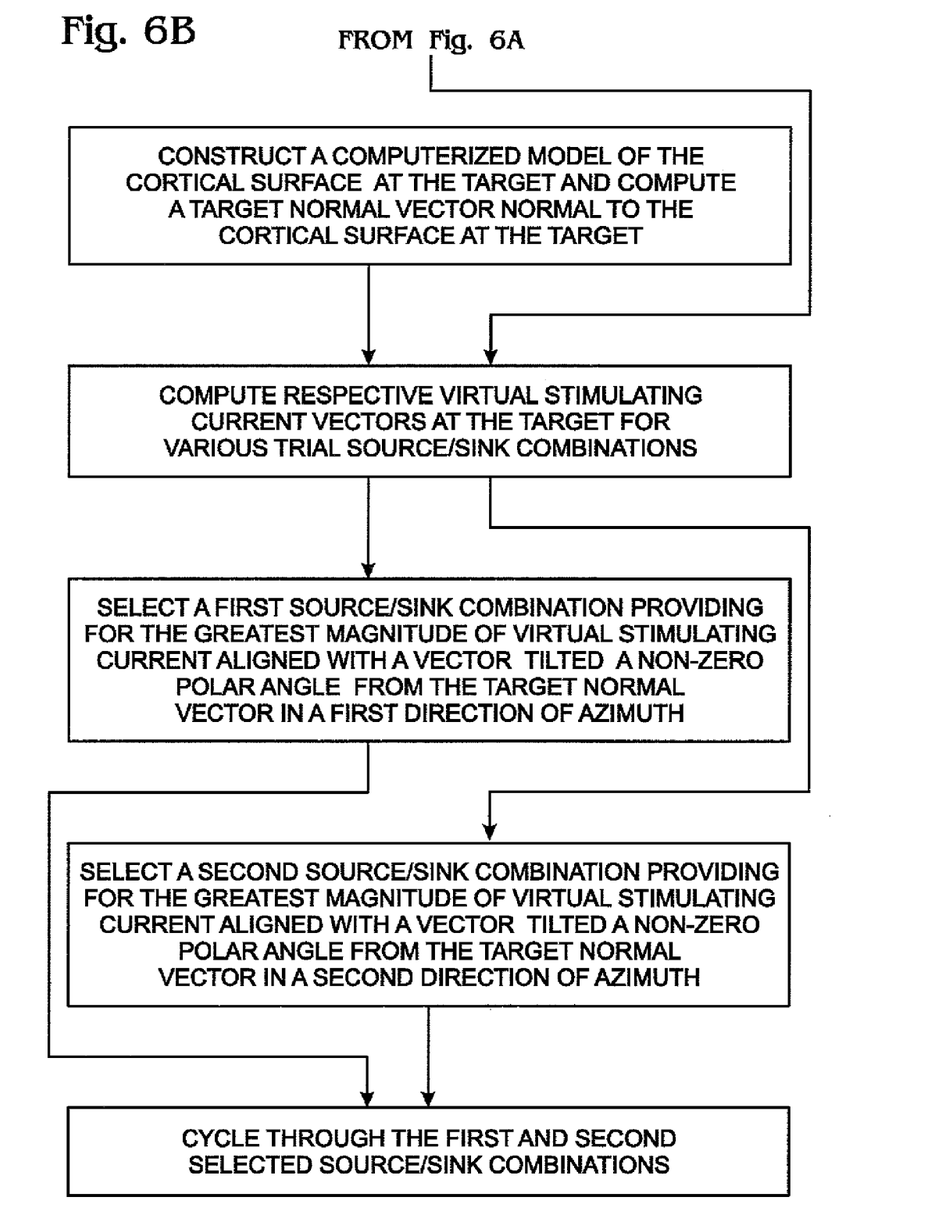
FIG. 6B is a continuation of FIG. 6A.

A fourth computational method 40 for determining how to stimulate a target patch of neurons on the cortical surface according to the present invention is based on a modification of the basic method 10 combined with the cycling feature of the method 30. As noted above, the basic method 10 optimizes the magnitude of the virtual stimulating current at the target patch which is aligned normal to the cortex at that location. In the method 40, a set of source/sink patterns is obtained for cycling as described for the method 30, except that in the method 40, each member of the set is optimized for maximizing the magnitude of the virtual stimulating current that is tilted from the normal to the cortical surface at the target location, by a small angle and in a particular direction, as an alternative to being optimized in consideration of balancing the impact of virtual stimulating currents on target and non-target areas as in the method 20.

FIGS. 6A and 6B are a flow chart showing how the method 40 applies in a simple case where there are two members in the set of trial dispositions, it being understood that the method employs the same steps if the sets of trial dispositions have more than two members.

The angle of tilt (or polar angle in a spherical coordinate system taking the normal to the cortical surface at the target location as the zenith direction) is preferably within the range of 5 to 45 degrees, more preferably in the range 5 to 30 degrees, and still more preferably in the range 10 to 20 degrees, and may be different for each member of the set. Where the angle is the same for all the source/sink patterns in the set, the members of the set correspond to unique directions of the tilt (or angles of azimuth in the same spherical coordinate system) which can be visualized as rays on the surface of a cone centered about the target normal and lying in planes with the target normal. Each source/sink pattern comes close to maximizing the dot product of the stimulating current and the normal vector at the target patch (e.g., the cosine of 20 degrees at 0.939 is close to 1), with the randomized directions providing for randomizing and thereby tending to reduce the stimulating effects on non-target patches.

Figure 7:
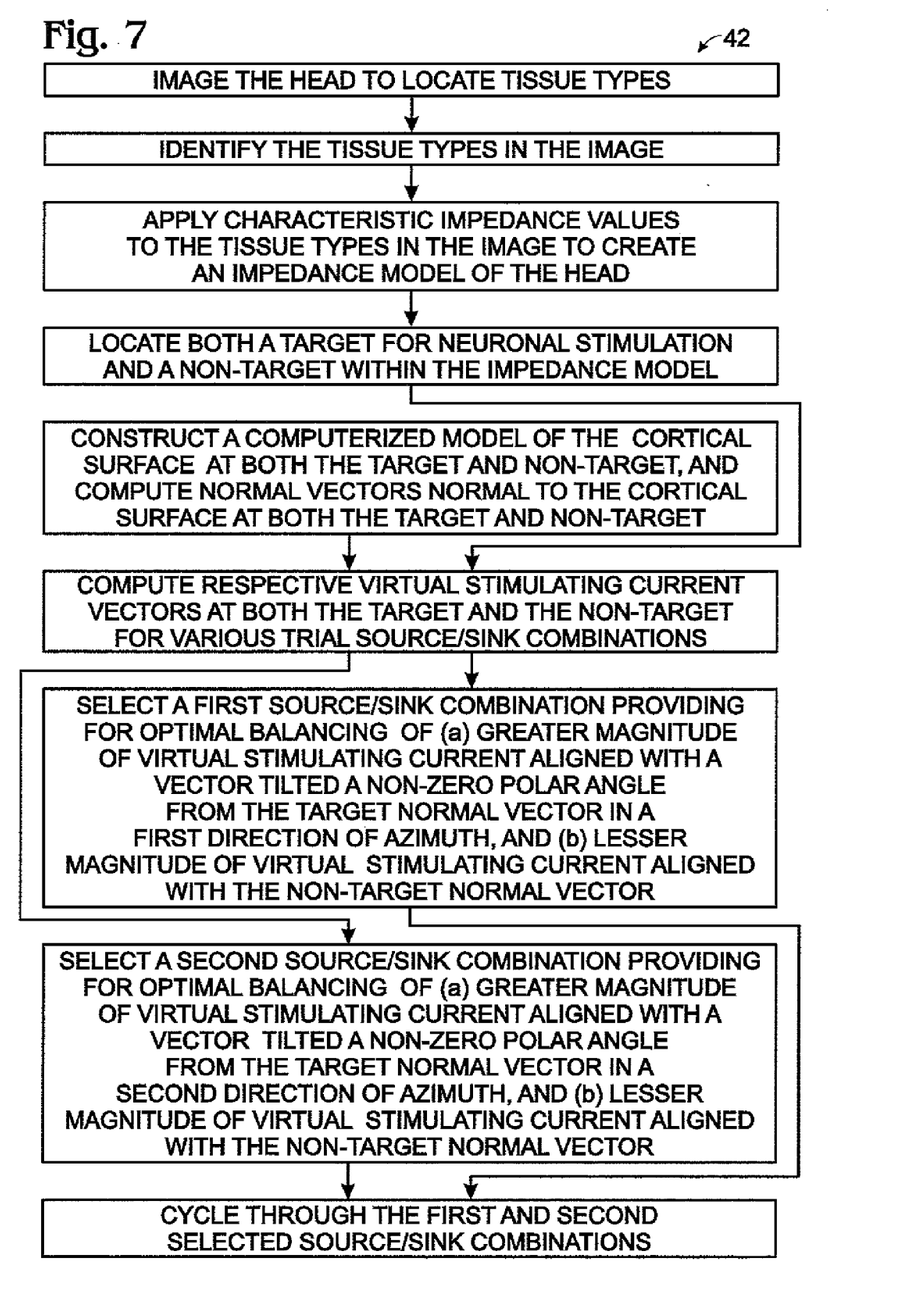
FIG. 7 is a flow chart of the first computational method of FIG. 3 modified according to the invention to incorporate principles of the second computational method of FIG. 4.

While as noted above in the method 40 each member of the set is optimized for maximizing the magnitude of the virtual stimulating current that is tilted from the normal to the cortical surface at the target location as an alternative to being optimized in consideration of balancing the impact of virtual stimulating currents on target and non-target areas as in the method 20, the method 40 may be used in combination with such balancing optimization. FIG. 7 is a flow chart showing a modified version 42 of the method 40 as an example.

As noted previously, all features of the invention described above in the context of TCS may be employed in TMS methods as well.

It is to be understood that, while a specific method for transcranial neurostimulation has been shown and described as preferred, other methods in accordance with the principles described herein could be utilized without departing from the principles of the invention.

The terms and expressions which have been employed in the foregoing specification are used therein as terms of description and not of limitation, and there is no intention in the use of such terms and expressions to exclude equivalents of the features shown and described or portions thereof, it being recognized that the scope of the invention is defined and limited only by the claims which follow.

The invention claimed is:

1. A method for determining how to stimulate a target patch of neurons in a subject's brain and stimulating the same, comprising:

obtaining an impedance model of the brain, and identifying within the impedance model a target location corresponding to the target of neurons;

obtaining a device model of a predetermined device capable of producing electric or magnetic fields outside the brain;

using the device model and the impedance model to compute a first virtual target stimulating current vector at the target location resulting from virtually using the device as disposed in a first trial disposition outside the brain to produce a virtual electric or magnetic field, and a second virtual target stimulating current vector at the target location resulting from virtually using the device as disposed in a second trial disposition outside the brain distinct from the first trial disposition to produce a virtual electric or magnetic field;

obtaining an image of the cortical surface of the brain at the target location and using the image for computing a target normal vector normal to the cortical surface at the target location; and determining which of the first and second virtual target stimulating current vectors has a greater component of virtual target stimulating current projecting at a predetermined first polar angle between zero and 45 degrees with reference to a spherical coordinate system taking the direction of the target normal vector as the zenith direction; and selecting one of the first and second trial dispositions; and stimulating the target patch of neurons comprising actually using the device in the selected trial disposition to produce a real electric or magnetic field.

2. The method of claim 1, wherein the first polar angle is zero.

3. The method of claim 2, wherein the step of selecting is based, at least in part, on favoring that one of the first and second virtual target stimulating current vectors which has the greater said component of target stimulating current.

4. The method of claim 2, wherein the image includes a first non-target at a first non-target location distinct from the target location, the method further comprising using the device model and the impedance model to compute a first virtual "first non-target" stimulating current vector at the first non-target location resulting from virtually using the device as disposed in the first trial disposition, and a second virtual "first non-target" stimulating current vector at the first non-target location resulting from virtually using the device as disposed in the second trial disposition, wherein the method further comprises using the image for computing a "first-non target" normal vector normal to the cortical surface at the first non-target location, and determining which of the first and second virtual "first non-target" stimulating current vectors has a lesser component of virtual "first non-target" stimulating current projecting parallel to the "first non-target" normal vector.

5. The method of claim 4, wherein said step of selecting between the first and second trial dispositions of the device is based, at least in part, on balancing between favoring that one of the first and second virtual target stimulating current vectors which has the greater said component of virtual target stimulating current and favoring that one of the first and second virtual "first non-target" stimulating current vectors which has the lesser said component of virtual "first non-target" stimulating current.

6. The method of claim 4, further comprising using the device model and the impedance model to compute a first virtual "second non-target" stimulating current vector at a second non-target location distinct from the target location and the first non-target location resulting from virtually using the device as disposed in the first trial disposition, and a second virtual "second non-target" stimulating current vector at the second non-target location resulting from virtually using the device as disposed in the second trial disposition, wherein the image includes the second non-target and the method further comprises using the image for computing a "second non-target" normal vector normal to the cortical surface at the second non-target location, determining which of the first and second virtual "second non-target" stimulating current vectors has a lesser component of virtual "second non-target" stimulating current projecting parallel to the "second non-target" normal vector, wherein said step of selecting between the first and second trial dispositions of the device is based, at least in part, on balancing between favoring that one of the first and second virtual target stimulating current vectors which has the greater said component of virtual target stimulating current and favoring that one of the first and second virtual "second non-target" stimulating current vectors which has the lesser said component of virtual "second non-target" stimulating current, the method further providing for stimulating the target patch of neurons comprising actually using the device at the selected trial disposition to produce a real electric or magnetic field over a first time period, and actually using the device at the second selected trial disposition to produce a real electric or magnetic field over a second time period distinct from the first time period.

7. A method for determining how to stimulate a target patch of neurons in a subject's brain and stimulating the same, comprising:

obtaining an impedance model of the brain, and identifying within the impedance model a target location corresponding to the target of neurons;

obtaining a device model of a predetermined device capable of producing electric or magnetic fields outside the brain;

using the device model and the impedance model to compute a first virtual target stimulating current vector at the target location resulting from virtually using the device as disposed in a first trial disposition outside the brain to produce a virtual electric or magnetic field, and a second virtual target stimulating current vector at the target location resulting from virtually using the device as disposed in a second trial disposition outside the brain distinct from the first trial disposition to produce a virtual electric or magnetic field;

obtaining an image of the cortical surface of the brain at the target location and using the image for computing a target normal vector normal to the cortical surface at the target location;

determining which of the first and second virtual target stimulating current vectors has a greater component of virtual target stimulating current projecting at a predetermined first polar angle between five and 45 degrees with reference to a spherical coordinate system taking the direction of the target normal vector as the zenith;

selecting between the first and second trial dispositions of the device based, at least in part, on favoring that one of the first and second virtual target stimulating current vectors which has a greater component of target stimulating current projecting at said first polar angle at a predetermined first angle of azimuth in said spherical coordinate system;

using the device model and the impedance model to compute a third virtual target stimulating current vector at the target location resulting from virtually using the device as disposed in a third trial disposition outside the brain distinct from the first and second trial dispositions to produce a virtual electric or magnetic field, and a fourth virtual target stimulating current vector at the target location resulting from virtually using the device as disposed in a fourth trial disposition outside the brain distinct from the first, second, and third trial dispositions to produce a virtual electric or magnetic field;

selecting between the third and fourth trial dispositions of the device based, at least in part, on favoring that one of the third and fourth virtual target stimulating current vectors which has a greater component of virtual target stimulating current projecting at a predetermined second polar angle of at least 5 degrees but less than or equal to 45 degrees at a second angle of azimuth in said spherical coordinate system distinct from the first angle of azimuth; and actually using the device at the selected one of the first and second trial dispositions to produce a real electric or magnetic field over a first time period, and actually using the device at the selected one of the third and fourth trial dispositions to produce a real electric or magnetic field over a second time period distinct from the first time period.

8. The method of claim 7, wherein the image includes a first non-target at a first non-target location distinct from the target location, the method further comprising using the device model and the impedance model to compute a first virtual non-target stimulating current vector at the non-target location resulting from virtually using the device as disposed in the first trial disposition, and a second virtual non-target stimulating current vector at the non-target location resulting from virtually using the device as disposed in the second trial disposition, wherein the the method further comprises using the image for computing a non-target normal vector normal to the cortical surface at the non-target location, and determining which of the first and second virtual non-target stimulating current vectors has a lesser component of virtual non-target stimulating current projecting parallel to the non-target normal vector, wherein said step of selecting between the first and second trial dispositions of the device is based in part on balancing between favoring that one of the first and second virtual target stimulating current vectors which has the greater said component of target stimulating current projecting at said first polar angle at a predetermined first angle of azimuth, and favoring that one of the first and second virtual target stimulating current vectors which has the lesser said component of virtual non-target stimulating current.

* * * * *